US011772141B1

(12) United States Patent
Li et al.

(10) Patent No.: US 11,772,141 B1
(45) Date of Patent: Oct. 3, 2023

(54) METHOD FOR TARGETED REGULATION OF SOIL MICROBES TO SYNCHRONIZE HEAVY METAL/METALLOID TRANSFORMATION AND GREENHOUSE GAS EMISSION REDUCTION AND USE

(71) Applicant: Institute of Eco-environmental and Soil Sciences, Guangdong Academy of Sciences, Guangzhou (CN)

(72) Inventors: Fangbai Li, Guangzhou (CN); Liping Fang, Guangzhou (CN)

(73) Assignee: Institute of Eco-Environmental and Soil Sciences, Guangdong Academy of Sciences, Guangdong (CN)

( * ) Notice: Subject to any disclaimer, the term of this patent is extended or adjusted under 35 U.S.C. 154(b) by 0 days.

(21) Appl. No.: 17/961,276

(22) Filed: Oct. 6, 2022

(30) Foreign Application Priority Data

Apr. 18, 2022 (CN) .......................... 202210401561.7

(51) Int. Cl.
  *B09C 1/10* (2006.01)
  *B09C 1/08* (2006.01)
  *C12N 1/20* (2006.01)
  *C09K 17/14* (2006.01)
  *C12R 1/145* (2006.01)

(52) U.S. Cl.
  CPC ................ *B09C 1/08* (2013.01); *C09K 17/14* (2013.01); *C12N 1/205* (2021.05); *B09C 2101/00* (2013.01); *C12R 2001/145* (2021.05)

(58) Field of Classification Search
  None
  See application file for complete search history.

(56) References Cited

FOREIGN PATENT DOCUMENTS

| CN | 1806952 A | 7/2006 |
|----|-----------|--------|
| CN | 105524623 A | 4/2016 |

(Continued)

OTHER PUBLICATIONS

'Principle and technique of arsenic and cadmium pollution control in paddy field', Authors: Yu Huan-yun, Cui Jiang-hu, Qiao Jiang-tao, Liu Chuan-ping, Li Fang-bai; Journal of Agro-Environment Science, 2018, 37(7): 1418-1426.

(Continued)

*Primary Examiner* — David W Berke-Schlessel
(74) *Attorney, Agent, or Firm* — Reising Ethington P.C.

(57) ABSTRACT

The present disclosure discloses a method for targeted regulation of soil microbes to synchronize heavy metal/metalloid transformation and greenhouse gas emission reduction and use. The present disclosure discovers that by compounding methionine with an organic acid salt, the obtained formulation can significantly increase the ability of the soil microbes to promote arsenic methylation in a targeted mode, and meanwhile, and the methane production is effectively reduced in the presence of the methionine. In the present disclosure, the methionine/organic acid salt formulation is further loaded into a modified biochar material of a porous structure, so as to achieve the effect of slow release. The method of the present disclosure may effectively reduce absorption of inorganic arsenic by rice, achieve a significant reduction in the proportion of inorganic arsenic in the total arsenic in the rice and inhibit methane emission of the soils and reduce methane emission at the same time.

6 Claims, 8 Drawing Sheets

Specification includes a Sequence Listing.

(56) References Cited

FOREIGN PATENT DOCUMENTS

| | | | |
|---|---|---|---|
| CN | 108157596 A | * | 6/2018 |
| CN | 108772418 A | | 11/2018 |
| CN | 112845564 A | | 5/2021 |

OTHER PUBLICATIONS

"Functional and unique diversities of genes and microorganism involved in redox reactions of arsenic from the severely-contaminated soils", Author: Yahaya Kudush Kawa, <Full Text Database of Chinese Doctoral Dissertations (Part I of Engineering Science and Technology)>, 2020 , B027-14.

Notification to Grant Patent Right for Invention Regarding CN202210401561.7, dated Aug. 23, 2022.

* cited by examiner

METHOD FOR TARGETED REGULATION OF SOIL MICROBES TO SYNCHRONIZE HEAVY METAL/METALLOID TRANSFORMATION AND GREENHOUSE GAS EMISSION REDUCTION AND USE

REFERENCE TO AN ELECTRONIC SEQUENCE LISTING

The contents of the electronic sequence listing (NEWP22GZ1NW00146USSeqList.xml; Size: 6,079 bytes; and Date of Creation: Aug. 31, 2022) is herein incorporated by reference in its entirety.

CROSS-REFERENCE TO RELATED APPLICATION

The present disclosure is based on and claims the priority of the Chinese Patent Application No. 202210401561.7, filed on Apr. 18, 2022, the entire contents of which are incorporated herein by reference.

TECHNICAL FIELD

The present disclosure covers the technical fields of microorganisms and contaminated soil remediation, and in particular relates to a method for targeted regulation of soil microbes to synchronize heavy metal/metalloid transformation and greenhouse gas emission reduction and use.

BACKGROUND

Soils of rice fields play an important function of food production and are a non-renewable resource that supports survival of human beings in the world. However, due to the double cumulated influence of high-intensity human activities and high geological background, the problem of heavy metal/metalloid (such as cadmium and arsenic) contamination in the soils of the rice fields is prominent, which leads to excessive heavy metals/metalloid accumulate in rice and threatens human health. At the same time, the rice fields are a typical type of constructed wetlands and are an important emission source of greenhouse gas, especially methane. The warming effect of methane is reported to be 25 times that of carbon dioxide. Therefore, effective reduction of greenhouse gas emission in the soils of the rice fields has an important contribution to achieving a carbon neutrality goal, in premise of achieving heavy metal/metalloid/contamination control and food safety production. Therefore, exploring a technical strategy that may systematically achieve the above goals will be of great significance to ensure the sustainable production of rice fields in the world and curb climate changes.

At present, remediation of heavy metal/metalloid contaminated soils of the rice fields is mainly based on two methods, namely removal and immobilization, thereby reducing risks. The engineering measures mainly include the imported soil method, soil replacement and turning, topsoil removal and other measures, which are based on the characteristic that heavy metal/metalloid contamination of the soils is generally concentrated in a soil surface layer. With high engineering work amount, high investment cost, damages to the soil structure and decrease in soil fertility, the current remediation is only suitable for remediation of a small area of severely contaminated soils. Besides, a lot of energy is consumed, which is not conducive to emission reduction of greenhouse gas and is not sustainable. The fixation and stabilization technology mainly realizes stabilization of cadmium and arsenic in soils by applying inorganic mineral materials, such as Chinese patent CN201710413193, using composites such as lime and humus to increase a pH value and organic matter content of the soils. The Chinese patent CN201710243623.5 uses straws and ferric salt to prepare a biochar material for heavy metal (metalloid) contaminated soils, while the biochar material has an application amount reaching 22.5-67.5 t/hm$^2$ and cannot be used for large-scale farmland treatment due to too large application amount. The applicant' previous Chinese patent ZL201810816810.2 combines peat soils and other matter with iron powder, ferrous salt, etc., to obtain a cadmium-arsenic synchronous passivation agent of a three-layer structure, which realized synchronous and efficient passivation of the arsenic and the cadmium. However, on the one hand, the above technologies mainly only consider the stabilization performance and application of heavy metals/metalloid, but do not involve the impact of emission of the greenhouse gas. Existing studies have shown that peat is more conducive to methane emission, but not conducive to emission reduction of the greenhouse gas (Pedosphere 2009, 19: 409-421). On the other hand, in view of the problem of arsenic contamination in the soils, since organic arsenic is non-toxic, the restrictions on the arsenic in food standards are often based on inorganic arsenic, and the above technologies mainly realize oxidation and adsorption fixation of the arsenic through physical and chemical effects, which cannot effectively reduce the proportion of the inorganic arsenic with higher toxicity in total arsenic in rice. Therefore, while reducing the total amount, reducing the proportion of the inorganic arsenic is also the key to reduce the health risk of the arsenic in the rice.

To sum up, the multi-target coordinated governance of how to effectively reduce the activity of the heavy metals/metalloidsin the soils to finally achieve the standard of the heavy metals in the rice and emission reduction of the greenhouse gas is still a major technical challenge currently facing.

SUMMARY

The primary object of the present disclosure is to overcome the deficiencies and shortcomings of the prior art, and to provide a method for targeted regulation of soil microbes to synchronize heavy metal/metalloid transformation and greenhouse gas emission reduction.

Another object of the present disclosure is to provide a formulation for targeted regulation of soil microbes to synchronize heavy metal/metalloid transformation and greenhouse gas emission reduction.

Yet another object of the present disclosure is to provide a preparation method for the above-mentioned formulation for targeted regulation of soil microbes to synchronize heavy metal/metalloid transformation and greenhouse gas emission reduction.

The objects of the present disclosure can be achieved through the following technical solutions:

a method for targeted regulation of soil microbes to synchronize heavy metal/metalloid transformation and greenhouse gas emission reduction, comprising placing a formulation comprising methionine (Met) and organic acid salt (Fat) in arsenite and/or arsenate contaminated soils simultaneously to achieve arsenic methylation and methane emission reduction synchronously.

Further, the organic acid salt is at least one of acetate (Ace), lactate (Lac) or butyrate (But) of sodium, potassium and calcium. All salt used in the embodiments of the present disclosure is sodium salt.

Further, a molar ratio of the methionine to the organic acid salt is (1:5)-(1:50); preferably 1:10.

Further, an adding amount of the methionine is 0.5-1.5 mM based on its concentration in a reaction system; preferably 1 mM.

Further, the methylation is at least one of monomethylation, dimethylation or trimethylation.

Further, the soils are rice field soils.

A formulation for targeted regulation of soil microbes to synchronize heavy metal/metalloid transformation and greenhouse gas emission reduction is provided, which is a formulation comprising methionine and the organic acid salt described in the above method.

A preparation method for the above-mentioned formulation for targeted regulation of the soil microbes to synchronize heavy metal/metalloid transformation and greenhouse gas emission reduction is provided, which is Method I or Method II as below:

Method I: mixing methionine and an organic acid salt directly; and

Method II: loading methionine and the organic acid salt into a porous biochar material.

Further, the porous biochar material has a large specific surface area and is prepared by a following method, which includes the following steps:

step 1: crushing a biomass raw material, preferably balsa wood into particles with a particle size being less than 2 mm, washing and drying;

step 2: putting the particles prepared in step 1 in a vacuum tube furnace, heating to 500-1100° C., preferably 800° C., under the protection of nitrogen or inert gas, and keeping for 1-3 hours to prepare a pre-treated porous biochar material (BC); and step 3: soaking the pre-treated porous biochar material prepared in step 2 into a Tri-HCl buffer containing dopamine, or into a Tri-HCl buffer containing the dopamine and cysteine for reaction, to obtain the porous biochar material (BC-PDP and BC-PDP-S). The cysteine is added for formation of thiol functional groups in the process that the cysteine forms polymeric dopamine (PDP) on the surface of BC.

Further, the washing and drying described in step 1 includes the following specific steps: soaking the obtained particles into a mixed solution of 2.5 M NaOH, 0.4 M $Na_2SO_3$ and 2.5 M $H_2O_2$, stirring evenly, transferring to a reaction kettle, and keeping at 100° C. for 10 h.

Further, a concentration of the Tri-HCl buffer described in step 3 is 10 mM, and a pH value is 7.5±0.2.

Further, concentrations of the dopamine and the cysteine in the reaction system described in step 3 are both 0.5-1.5 mM; preferably 1 mM.

Further, the reaction condition described in step 3 is stirring for reaction for 50-70 min; preferably, stirring for reaction for 60 min.

Further, Method I includes the specific steps: mixing methionine and the organic acid salt in a mixed solution of sodium hydrogen phosphate, magnesium chloride, calcium chloride and ammonium chloride in proportion.

Further, Method II includes the specific steps: after the porous biochar material is obtained, adding methionine and the organic acid salt directly for stirring, so that methionine and the organic acid salt are fully adsorbed into the porous biochar material to form a composite system; and drying, to obtain the formulation for targeted regulation of soil microbes to synchronize heavy metal/metalloid transformation and greenhouse gas emission reduction.

Further, the concentrations of methionine and the organic acid salt in the reaction system are calculated such that the molar ratio of the methionine and the organic acid salt in the formed composite system is (1:5)-(1:50), preferably 1:10.

In the formulation for targeted regulation of the soil microbes to synchronize heavy metal/metalloid transformation and greenhouse gas emission reduction obtained in the preferred embodiments of the present disclosure, the weights of Met and Fat in Met/Fat@BC-PDP account for 20.5% of the total weights, and the weights of Met and Fat in Met/Fat@BC-PDP-S account for 19.8% of the total weights.

Use of the above-mentioned formulation for targeted regulation of the soil microbes to synchronize heavy metal/metalloid transformation and greenhouse gas emission reduction, comprising placing the formulation and *Clostridium* bacteria in arsenite and/or arsenate-contaminated soils simultaneously to achieve arsenic methylation and methane emission reduction synchronously.

Further, the *Clostridium* bacteria is *Clostridium sporogenes*, preferably *Clostridium sporogenes* LHA6. This *Clostridium sporogenes* LHA6 were deposited in Guangdong Microbial Culture Collection Center (GDMCC) (at Building 59, Yard No. 100, Xianlie Middle Road, Yuexiu District, Guangzhou City, Guangdong Province), China on Jan. 14, 2022, with the deposit number: GDMCC No: 62212. The *Clostridium sporogenes* LHA6 is a *Clostridium sporogenes* which has a function of fermentative hydrogen production and anaerobic arsenic methylation simultaneously.

Further, the adding amount of the *Clostridium* bacteria is calculated such that a bacterial cell density $OD_{600}$ in the reaction system is 0.1.

A compound formulation for targeted regulation of soil microbes to synchronize heavy metal/metalloid transformation and greenhouse gas emission reduction, including the above-mentioned preparation and *Clostridium* bacteria.

Compared with the prior art, the present disclosure has the following advantages and effects:

Met is an effective methyl donor, which can effectively promote methylation reactions involving DNA, arsenic, mercury, a protein, etc., but the Met lacks effective targeting and selectivity, decomposes rapidly in the environment and is insufficient in long-term effect. According to the present disclosure, by compounding the Met with a specific organic acid salt (specifically, acetate, lactate and butyrate) according to a specific ratio, the obtained formulation can significantly increase the ability of the soil microbes to promote arsenic methylation in a targeted mode, and meanwhile, the methane production is effectively reduced in the presence of the Met. In particular, when combination modes of Met+Ace and Met+Lac are selected, the methane emission is lower than that of a control group (i.e., an arsenic-contaminated soil system without Met added), which significantly reduces and inhibits soil methane emission.

The present disclosure further constructs Met/Fat@BC-PDP-S and Met/Fat@BC-PDP-S composites, in which the Met/Fat formulation is successfully loaded on a modified biochar material of a porous structure, so that the effect of slow release is achieved, and the problem of rapid decomposition of the Met in the soil system is effectively solved. By modifying the porous biochar materials with the dopamine, the affinity of Met/Fat on the surface of biochar is significantly improved, thereby greatly increasing the loading capacity of the porous biochar materials. Moreover, the two kinds of modified biochar materials are both capable of reducing methane emission of the soils. For mercury-arsenic-contaminated soils, the biochar material modified by cysteine and PDP can effectively inhibit methylation of mercury, better regulates arsenic methylation in a targeted mode, and inhibits occurrence of methylmercury while reducing the proportion of the inorganic arsenic.

In general, the formulation and the composite thereof of the present disclosure may effectively reduce absorption of the inorganic arsenic by the rice, achieve a significant reduction in the proportion of the inorganic arsenic in the total arsenic in the rice, and inhibits soil methane emission and reduces soil methane emission at the same time.

DETAILED DESCRIPTION

The present disclosure will be further described below in conjunction with embodiments and accompanying drawings, but the embodiments of the present disclosure are not limited thereto.

Embodiment 1: Comparison on Effects of Different Combinations of Fat and Met on Regulating Methane Emission and Arsenic Methylation in Soils 5 grams of arsenic-contaminated rice field soils taken from Hunan Province, China was placed into a 20 mL glass sample tube, 2.5 mL of sterilized culture medium was added, and then the glass sample tube was placed in an anaerobic glove box for cultivation. The culture medium was composed of 10 mM $NH_4Cl$, 5 mM $NaHCO_3$, 1 mM $KH_2PO_4$, 0.5 mM $MgCl_2$, 0.5 $CaCl_2$, 1 mL of $L^{-1}$ vitamin and 1 mL/L of trace elements. After anaerobic culture in the glove box for 15 days, different combinations of Fat and Met (namely Met treatment, Fat treatment and Met+Fat treatment) were added into the glass sample tube respectively, wherein Fat included formate, acetate, lactate, propionate and butyrate, the molar ratio of Met to Fat was 1:10, the concentration of Met was 1 mM. After addition of the Met and the Fat and after further reaction for 60 days, headspace gas was collected and measured by GC-TCD, a soil suspension was extracted, and ammonium dihydrogen phosphate was added to desorb adsorbed methyl arsenic. After the resulted soil suspension passed through a 0.22-micron membrane, methyl arsenic, including monomethylarsenic, dimethylarsenic and trimethylarsenic oxides, in a soil solution was measured by HPLC-ICPMS. After 15 days of anaerobic culture in the glove box, the system was left standing for 60 days without any treatment, and used as a control group.

Figure 1:
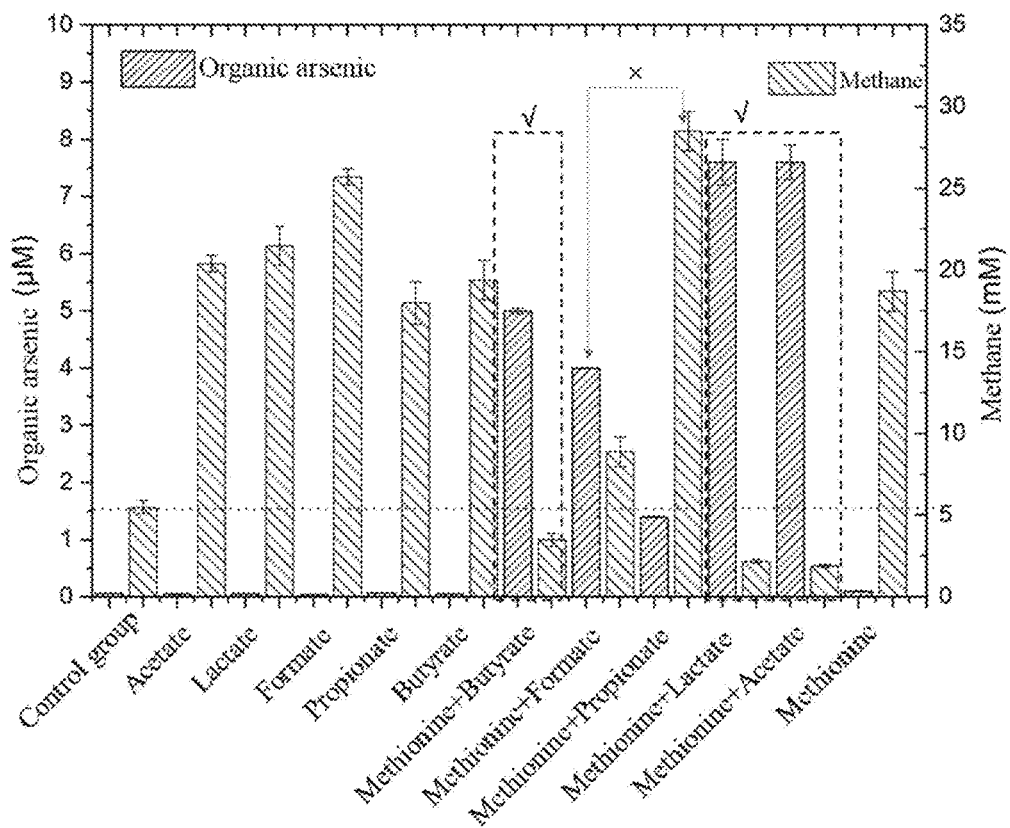
FIG. 1 is a statistical graph showing the methyl arsenic content and the methane emission in soils treated with different combinations of Fat and Met.

As can be seen from FIG. 1, production of methyl arsenic is mainly maintained at a level of 0.04-0.1 µM in a single Fat treatment group or a Met treatment group, and there is no significant difference compared with the control group (0.06 µM), while the yield of organic arsenic is greatly increased in a Fat and Met combined treatment group, all reaches 4.0-7.6 µM which is 57-152 times higher than that of the single treatment group, and the total arsenic methylation rate reaches 16% or above, except for combination of propionate and methionine (0.7 µM). The above results show that combination of Fat+Met may significantly increase production of methyl arsenic, wherein the combination of acetate or lactate and methionine has the highest transformation rate of methyl arsenic, while the combination of formate and methionine does not significantly promote production of the organic arsenic. In another aspect, for the production of methane, the single Fat or Met treatment group significantly improve the emission of methane in the soils, compared to 5.5 mM in the control group, the emission load is significantly increased to 18-25.7 mM with an increase by 3.3-4.7 times. In the Fat+Met combined treatment group, the methane emission of the three treatment groups of butyrate, lactate, acetate and methionine are 3.5 mM, 2.2 mM and 1.9 mM respectively, which are significantly lower than 5.5 mM in the control group, indicating that the three treatment groups may achieve emission reduction of the methane in the soils and simultaneously promote methylation of the arsenic in the soils, wherein the combination of acetate and methionine has the best effect. However, the combination of formate and methionine and the combination of propionate and methionine leads to a great increase in methane emission, and the synergy between methane emission reduction and arsenic methylation cannot be achieved.

On the basis of the above experimental results, the effects of treatments with the combinations of butyrate, lactate, acetate and methionine on arsenic-contaminated rice field soils taken from Chenzhou City, Hunan Province of China, Hechi City, Guangxi Province of China, and Shaoguan City, Guangdong Province of China were further evaluated. The results showed that the synergy between arsenic methylation and methane emission reduction was achieved.

Embodiment 2: Comparison on Effects of Different Ratios of Fat and Met on Regulating Methane Emission and Arsenic Methylation in Soils On the basis of Embodiment 1, the effects of the combination of acetate and methionine on methane emission and arsenic methylation under different molar ratios were evaluated. The mainly experimental scheme could be referred to Embodiment 1. After anaerobic cultivation of the soil suspension for 15 days, six treatments of methionine and butyrate or acetate in molar ratios of 0, 1:50, 1:25, 1:10, 1:5 and 1:1 were conducted, wherein the methionine concentration was 1 mM. After further anaerobic culture for 60 days, headspace gas was collected and measured by GC-TCD, a soil suspension was extracted, and ammonium dihydrogen phosphate was added to desorb adsorbed methyl arsenic. After the resulted soil suspension passed through a 0.22-micron membrane, the methyl arsenic in the soil solution was measured by HPLC-ICPMS.

Figure 2:
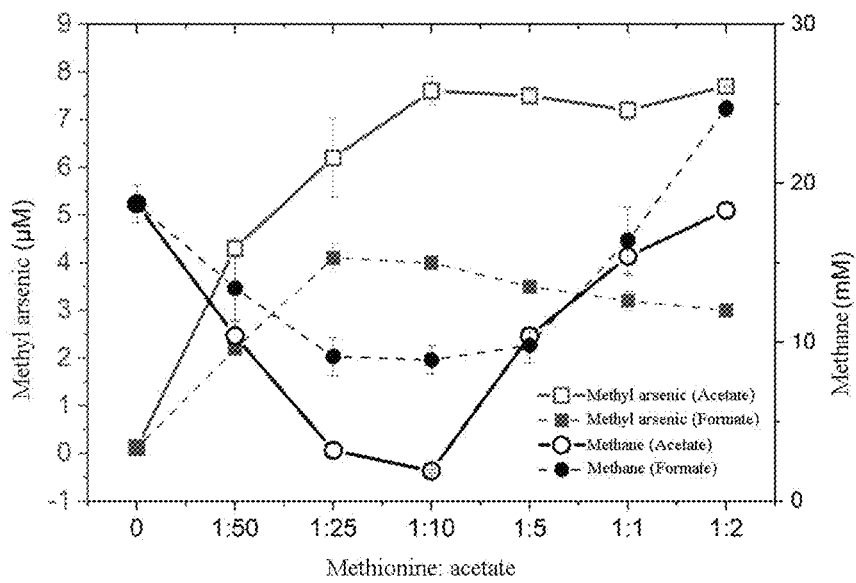
FIG. 2 is a statistical graph showing the methyl arsenic content and the methane emission in soils treated with different ratios of Met/Fat.

As can be seen from FIG. 2, as the molar ratio of acetate to methionine is increased from 0 to 1:10, the production of methyl arsenic in the soil suspension is gradually increased from 0.1 μM to 7.6 μM with an increase by 76 times. Further, with the increase of the molar ratio of the acetate, the production of the methyl arsenic is basically maintained at a level of 7.2-7.7 μM. For the production of methane, with the increase of the ratio of the acetate, the production of methane is gradually decreased from 18.7 mM in a single methionine treatment group to 1.9 mM under the ratio of 1:10, and with further increase of the acetate ratio to 1:2, the production of methane is rapidly increased to 18.3 mM. As a control, formate and methionine further have similar trends at different molar ratios. Although the combination of formate and methionine can promote the methylation of arsenic to a certain extent, the production of methane in this reaction system is far greater than the methane emission of the control group as shown in Embodiment 1, regardless of the set ratio range, and the synergy between methane emission reduction and arsenic methylation promotion cannot be achieved. It shows that the ratio of the organic acid salt to the methionine and the combination of the organic acid salt and the methionine all have important effects on the synergy of methane emission reduction and arsenic methylation promotion.

Embodiment 3: Analysis and Evaluation of Met/Fat on Regulating of Gene Expression and Biomass of Soil Functional Microbes For soil samples treated differently in the above-mentioned Embodiment 1 and Embodiment 2, RNeasy PowerSoil Total RNA Kit was used to extract total soil RNA; and after genomic DNA was removed, the RNA was reverse transcribed to synthesize double-stranded cDNA. cDNA was used to construct a functional gene PCR library, and then amplicon sequencing was performed to obtain a functional gene community structure and related microbial abundance. The absolute quantification of arsM and mcrA genes in cDNA was performed through a fluorescence quantitative PCR instrument (CFX 384 Real-Time PCR Detection System), wherein a primer used for arsM gene amplification was arsMF1/arsMR2 and had a fragment length of about 350 bp, and a primer for mcrA gene amplification was mlas/mcrA-rev and had a fragment length of about 450 bp; and the qPCR amplification system had a volume of 20 μL, including 10 μL of TB Green Premix Ex Taq master mix, 0.2 μM of upstream and downstream primers, 10 ng of cDNA template and RNA-free water. Construction of the plasmid standard was performed by ligating a vector pUC19 with a PCR product of arsM or mcrA gene. After a single clone was picked, plasmid DNA was extracted, the DNA concentration was measured with Qubit 3.0 Fluorometer, the gene copy number was calculated, and then the EASY dilution solution was diluted to $10^2$-$10^8$(copy number per μL) to obtain a Standard curve. Three replicates were set for all samples for fluorescence quantification and negative controls, the amplification efficiency was 90%-100%, and the correlation coefficient of the standard curve was greater than 0.9. Information and reaction procedures of the primers used for amplification of the arsM and mcrA genes were as follows:

arsMF1:  5'-TCYCTCGGCTGCGGCAAYCCVAC-3' (SEQ ID NO. 1)

arsMR2:  5'-CGWCCGCCWGGCTTWAGYACCCG-3' (SEQ ID NO. 2)

mlas: 5'-GGTGGTGTMGGDTTCACMCARTA-3' (SEQ ID NO. 3)

mcrA-rev:  5'-CGTTCATBGCGTAGTTVGGRTAGT-3' (SEQ ID NO. 4)

arsM amplification reaction program: at 95° C. for 10 min; at 95° C. for 30 s, at 60° C. for 45 s, and at 72° C. for 1 min, 40 cycles; and prolonging at 72° C. for 10 min;

mcrA amplification reaction program: at 95° C. for 10 min; at 95° C. for 15 s, at 58° C. for 30 s, and at 72° C. for 30 s, 40 cycles; and prolonging at 72° C. for 2 min.

Figure 3A:
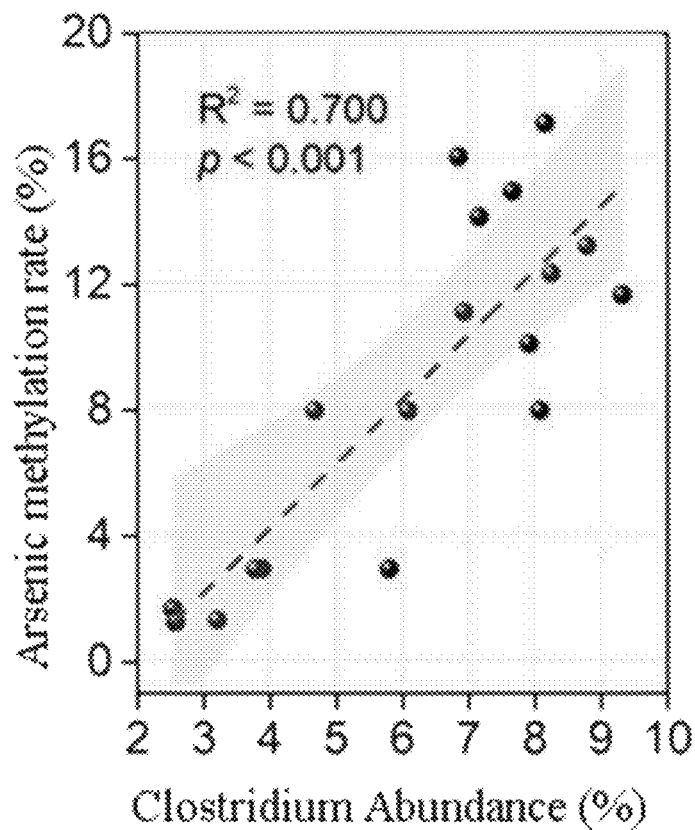
FIG. 3A is a graph showing a relationship between the abundance of *Clostridium* bacteria with an arsM gene and an arsenic methylation rate in soils treated with different combinations of Fat and Met.
Figure 3B:
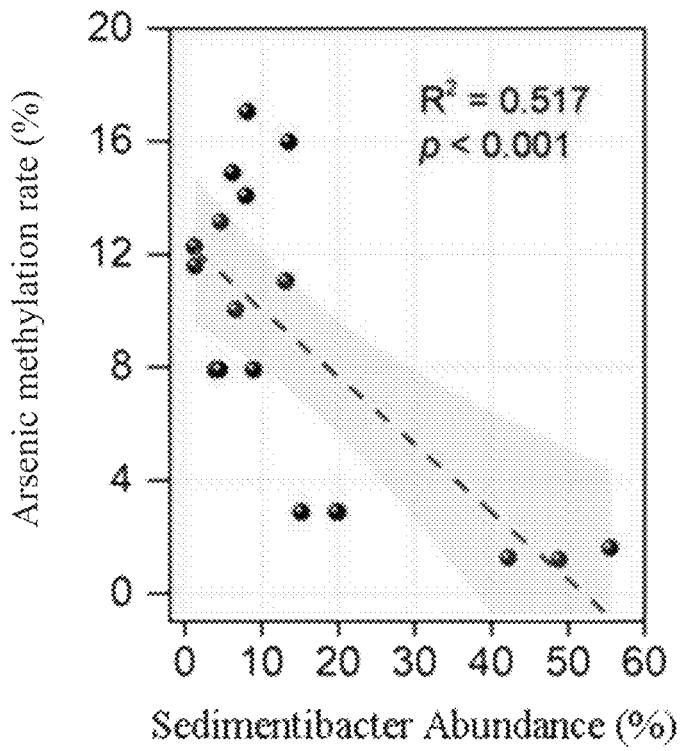
FIG. 3B is a graph showing a relationship between the abundance of *sedimentibacter* bacteria without an arsM gene and an arsenic methylation rate in soils treated with different combinations of Fat and Met.

The results show that in the soil control group, transcript copy numbers of the arsenic methylation gene arsM and the methanogenic gene mcrA are respectively 950 and $1.5*10^6$ copies per g of soils; while in the single methionine treatment group, the transcript copy numbers of arsM and mcrA are respectively 1200 and $2.0*10^7$ copies per g of soils, which are significantly increased compared with the control group; and in the mixed treatment group of acetate and methionine (with a molar ratio of 1:10), the transcript copy numbers of arsM and mcrA are respectively $1.8*10^4$ and $1.4*10^4$ copies per g of soils, which are increased by 18.9 and decreased by two orders of magnitude respectively compared with the soil control group, demonstrating that this treatment may achieve synchronization of up-regulation of arsenic methylation gene transcription and down-regulation of methanogenic transcription in soil microbial communities. As shown in FIG. 3A and FIG. 3B, through the combinations of different organic acids and the methionine, the abundance of *Clostridium* carrying the arsM gene in the soils may be up-regulated, thereby promoting arsenic methylation; and meanwhile, *Sedimentibacter* without the arsM gene may be down-regulated, so that the energy acquisition pathway and efficiency of soil methanogens making syntrophic cooperation with this type of bacteria are effectively reduced or even cut off, and then the activity of the soil methanogens and production and emission of the methane are inhibited. In particular, the combination of acetate and methionine may significantly increase the expression level of the arsM gene carrying the arsenic methylation functional gene, while maximally reduces the expression level of the methanogens mcrA gene.

Embodiment 4: Evaluation of Met/Fat and *Clostridium Sporogenes* LHA6 in Complex Regulation of Arsenic Methylation and Methane Emission Reduction in Soils The previously screened *Clostridium sporogenes* LHA6 carrying arsM gene is further combined with Met/Fat. This *Clostridium sporogenes* LHA6 was deposited in the Guangdong Microbial Culture Collection Center (GDMCC) Eat Building 59, Yard No. 100, Xianlie Middle Road, Yuexiu District, Guangzhou City, Guangdong Province), China , under the terms of the Budapest Treaty on Jan. 14, 2022, with the deposit number: GDMCC No: 62212. The *Clostridium sporogenes* LHA6 of the present invention can be in a biologically pure form. Referring to the experimental scheme of Embodiment 1, after anaerobic cultivation of the soil suspension for 15 days, exogenous arsenous acid was added to make a total arsenous acid (As(III)) content in the soil suspension reach 0.2 mM, and methionine and acetate were added at a molar ratio of 1:10, wherein the concentration of methionine was 1 mM; on the basis of the above treatment, a certain amount of the obtained bacteria solution of the LHA6 strain was added to make the OD600=0.1 in the reaction system. After further anaerobic culture for 60 days, headspace gas was collected and measured by GC-TCD, the soil suspension was extracted, and ammonium dihydrogen phosphate was added to desorb adsorbed methyl arsenic. After the resulted soil suspension passed through a 0.22-micron membrane, the methyl arsenic in the soil solution was measured by HPLC-ICPMS.

Figure 4:
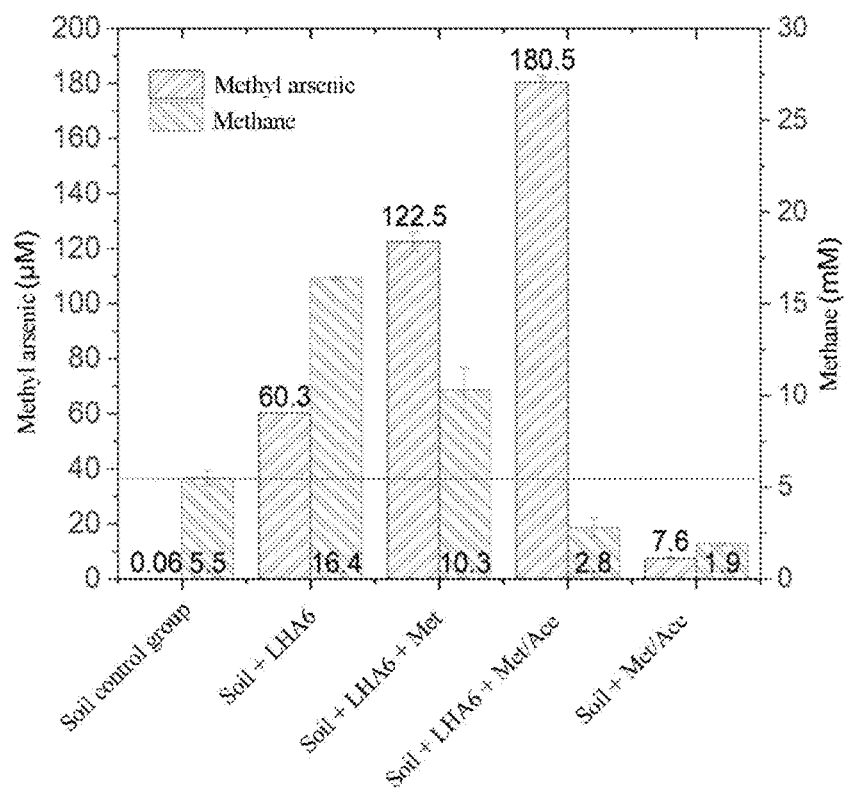
FIG. 4 is a statistical graph showing the methyl arsenic content and the methane emission in soils treated by Met/Fat and LHA6 strains jointly.

As shown in FIG. 4, in the LHA6 strain and Met/Ace treatment group, the yield of methyl arsenic in the soils reaches 180.5 μM, which is much higher than 122.5 μM in the LHA6 strain and Met treatment group and 60.3 μM in single LHA6 treatment; compared with the Met/Ace treatment group and single LHA6 treatment, the yield of the further combination of Met/Ace and the LHA6 strain is increased by 22.8 times and 2 times respectively, indicating that the combination of Met/Ace and LHA6 may significantly promote arsenic methylation in the soils. In another aspect, in single LHA6 treatment, methane emission is simultaneously increased to 16.4 mM; in the combination of LHA6 and Met, methane emission is further increased to 15.3 mM; while in the combination of Met/Ace and LHA6, the volume of the methane is significantly inhibited to 2.8 mM, which is only about 50% of that of 5.5 mM in the soil control. The above results show that with the combination of LHA6 and Met/Ace, the efficiency of arsenic methylation in the soils is significantly improved, and methane emission is well inhibited at the same time.

Embodiment 5: Preparation and Characterization of Met/Ace@BC-PDP and Met/Ace@BC-PDP-S Composites Step 1: balsa wood was crushed to obtain particles with a particle size being less than 2 mm, the particles were further soaked into 50 mL of a mixed solution of 2.5 M NaOH, 0.4 M $Na_2SO_3$ and 2.5 M $H_2O_2$ for even stirring, and a mixture was transferred to a reaction kettle and kept at 100° C. for 10 h.

Step 2: the pre-treated biomass powder particles were put in a vacuum tube furnace, and heated to 800° C. under the protection of nitrogen for 1 h for pyrolysis to obtain porous biochar material BC.

Step 3: the obtained porous biochar material BC was soaked into 50 mL of a Tri-HCl buffer containing 1 mM dopamine (a Tris-HCl concentration was 10 mmol/L, and a pH value was 7.5), and stirred for 1 hour for reaction to obtain a modified biochar material BC-PDP; taking the combination of acetate and methionine as an example, Met/Ace with a total molar concentration of 5 M and a molar ratio of about 1:10 was directly added, stirred for 1 h, centrifuged for removing water, and dried at a room temperature, to obtain the Met/Ace@BC-PDP composite.

The final molar ratio of the obtained Met/Ace was measured on HPLC and IC after extraction, and then the ratio of initial addition was adjusted, so that the Met/Ace with a molar ratio of 1:10 was finally obtained.

A porous biochar material BC was prepared by referring to steps 1-2. The obtained porous biochar material BC was soaked into 50 mL of a Tri-HCl buffer containing 1 mM dopamine and 1 mM cysteine (a Tris-HCl concentration was 10 mmol/L, and a pH value was 7.5), and stirred for 1 h for reaction to obtain a modified biochar material BC-PDP-S; taking the combination of acetate and methionine as an example, Met/Ace with a total molar concentration of 5 M and a molar ratio of about 1:10 was directly added, stirred for reaction for 1 h, centrifuged for removing water, dried at the room temperature, to obtain the Met/Ace@BC-PDP-S composite.

The final molar ratio of the obtained Met/Ace was measured on HPLC and IC after extraction, and then the ratio of initial addition was adjusted, so that the Met/Ace with a molar ratio of 1:10 was finally obtained.

Quantitative analysis results of Met/Ace@BC-PDP and Met/Ace@BC-PDP-S materials are as follows: in Met/Ace@BC-PDP, the Met content is 0.40 mmol/g, the Ace content is 3.10 mmol/g, and Met:Ace=0.13, in Met/Ace@BC-PDP-S, the Met content is 0.32 mmol/g, the Ace content is 2.80 mmol/g, and Met:Ace=0.11.

Figure 5A:
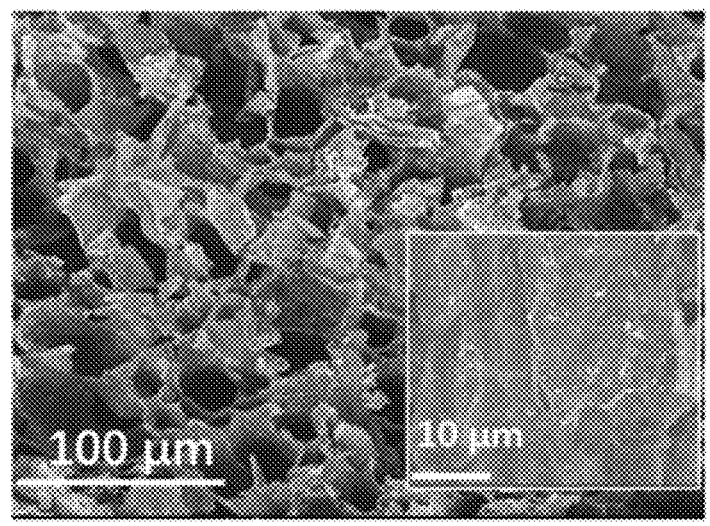
FIG. 5A shows the electron microscope images of Met/Ace@BC-PDP.
Figure 5B:
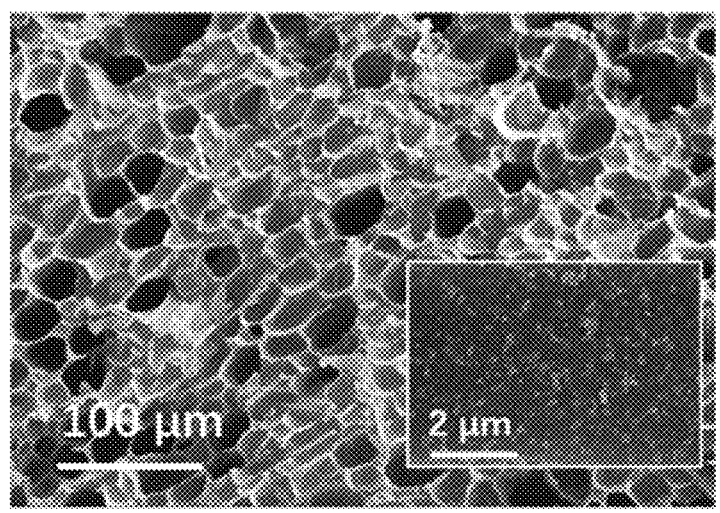
FIG. 5B shows the electron microscope images of Met/Ace @BC-PDP-S.
Figure 5C:
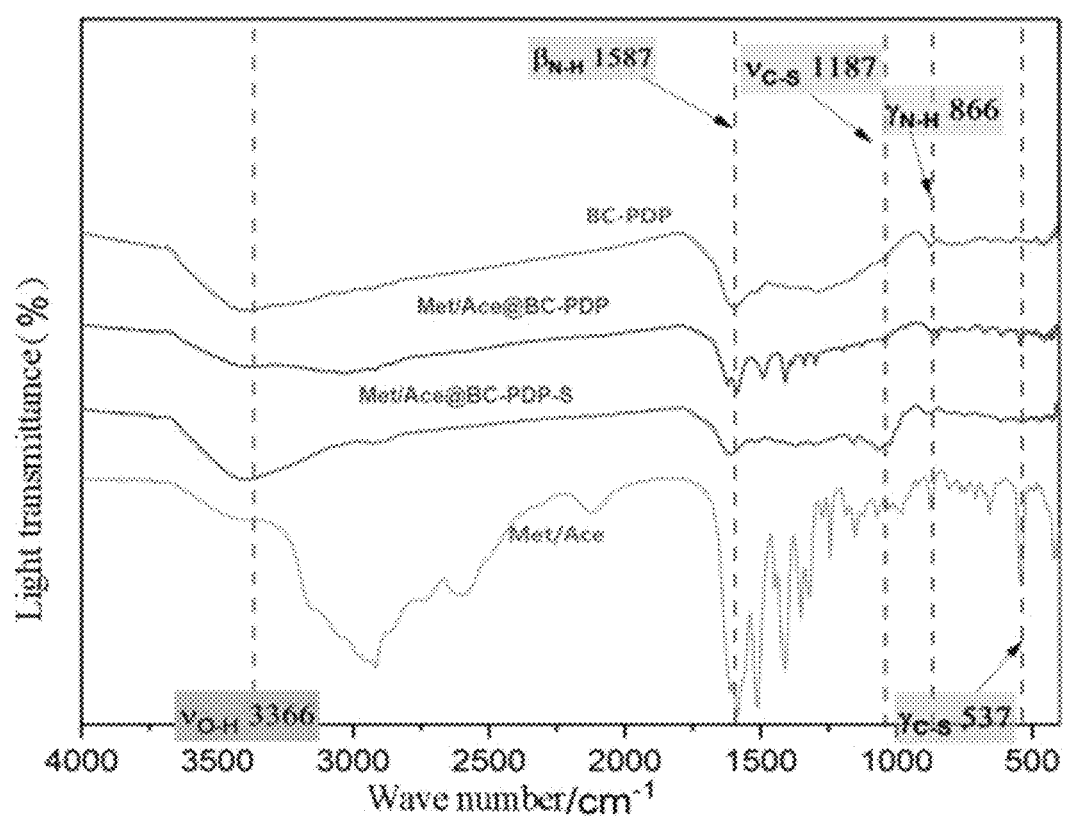
FIG. 5C shows the infrared spectrum of Met/Ace@BC-PDP composite and Met/Ace@BC-PDP-S composite.

As shown in FIG. 5A and FIG. 5B, both Met/Ace@BC-PDP and Met/Ace@BC-PDP-S have good porous structures. Combined with the further analysis of the infrared spectrum shown in FIG. 5C, it shows that the Met/Ace@BC-PDP and Met/Ace@BC-PDP-S materials have significant in-plane bending vibrations βN-H and γN-H at 1587 $cm^{-1}$ and 886 $cm^{-1}$, and these peaks are mainly from vibration of methionine or polymerized dopamine; and in addition, the Met/Ace@BC-PDP-S material has obvious vibration vc-s at 1187 $cm^{-1}$, which may be mainly derived from vibration peaks of cysteine.

Embodiment 6: Effect of Met/Ace@BC-PDP and Met/Ace@BC-PDP-S on Slow Release of Met in Soil Solution On the basis of the experimental scheme of Embodiment 1, the Met/Ace@BC-DP and Met/Ace@BC-PDP-S prepared in Embodiment 4 were used in a soil anaerobic culture system. After anaerobic cultivation of the soil suspension in a glove box for 15 days, the Met/Ace@BC-DP and Met/Ace@BC-PDP-S materials were added respectively with the adding amounts that the concentration of methionine in the system is 1 mM; anaerobic culture was further performed for 60 days; soil suspensions were collected at different time points, methanol and the like were added to desorb the methionine in the soils and the materials, then ultrasonic enhancement was performed; and after the resulted soil suspensions passed through a 0.22-micron membrane, contents of the methionine in the solutions were determined by HPLC.

Figure 6:
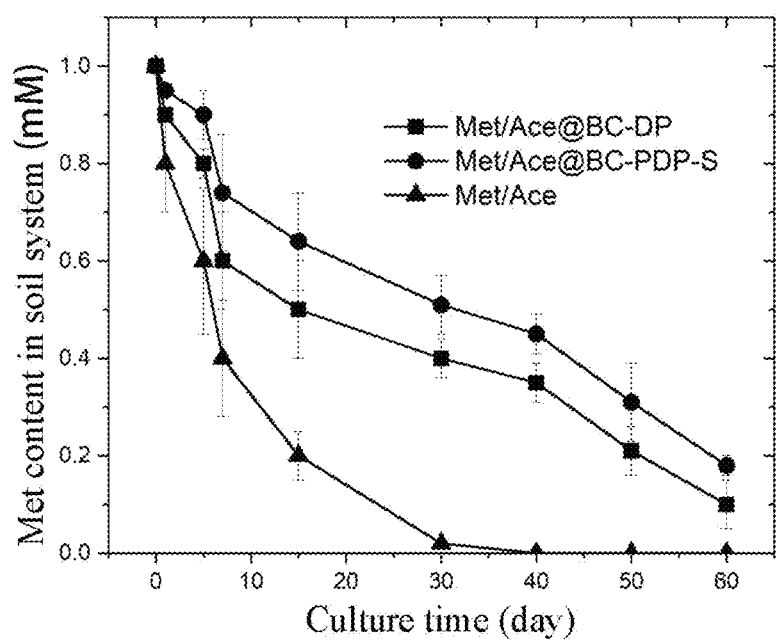
FIG. 6 is a diagram showing the effect of Met/Ace@BC-PDP and Met/Ace@BC-PDP-S on slow release of Met in a soil solution.

As can be seen from FIG. 6, in single Met/Ace mixture treatment, the content of Met is decreased rapidly with the reaction time and falls below a detection line after about 30 days. For the Met/Ace@BC-DP and Met/Ace@BC-DP-S materials, the release kinetics of Met is significantly prolonged, at the same 30-day culture time points, the Met contents in the Met/Ace@BC-DP and Met/Ace@BC-DP-S treatment group systems still reach up to 0.4 mM and 0.51 mM respectively. After 60 days of reaction, in the above two treatment groups, there are still 0.1 and 0.18 mM of Met, so that an existence time of Met in the soil system is significantly prolonged, showing a good slow-release effect.

Embodiment 7: Efficiency Evaluation of Met/Ace@BC-PDP and Met/Ace@BC-PDP-S in Regulating Arsenic Methylation and Reducing Methane Emission of Soils On the basis of the materials prepared in Embodiment 4, referring to the experimental scheme of Embodiment 1, some arsenic-mercury combined contaminated soil from Guizhou, China was taken, a soil suspension was anaerobically cultured in a glove box for 15 days, Met/Ace@

BC-PDP and Met/Ace@BC-PDP-S materials were added respectively with the adding amount that the concentration of methionine in the system was 1 mM. Anaerobic culture was further performed for 60 days, headspace gas was collected and measured by GC-TCD, a soil suspension was extracted, and ammonium dihydrogen phosphate was added to desorb adsorbed methyl arsenic. After the resulted soil suspension passed through a 0.22-micron membrane, methyl arsenic in a soil solution was measured by HPLC-ICPMS, and the analysis of methyl mercury was mainly based on gas chromatography cold vapor atomic fluorescence (GC-CVAFS).

Figure 7:
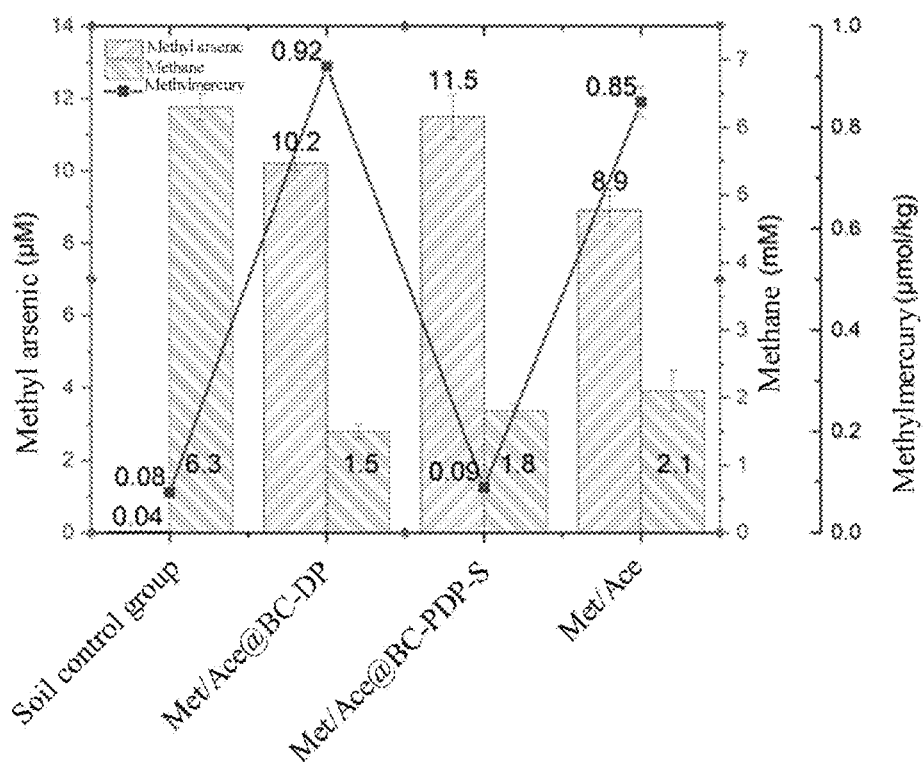
FIG. 7 is a statistical graph showing the methyl arsenic content and the methylmercury content in soils treated with Met/Ace@BC-PDP and Met/Ace@BC-PDP-S.
Figure 8A:
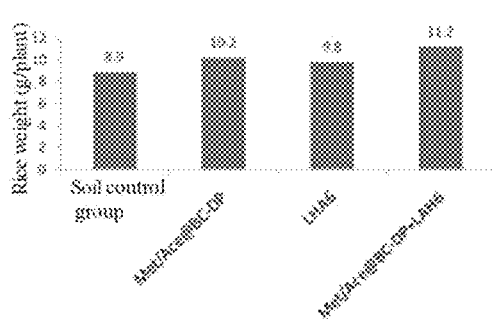
FIG. 8A shows the effect of the regulation of Met/Fat@BC-PDP combined with LHA6 strains on a weight of the rice.
Figure 8B:
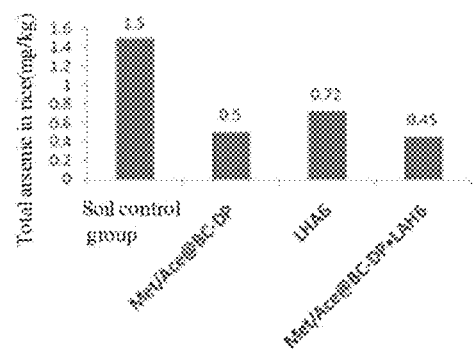
FIG. 8B shows the effect of the regulation of Met/Fat@BC-PDP combined with LHA6 strains on a total arsenic content of the rice.
Figure 8C:
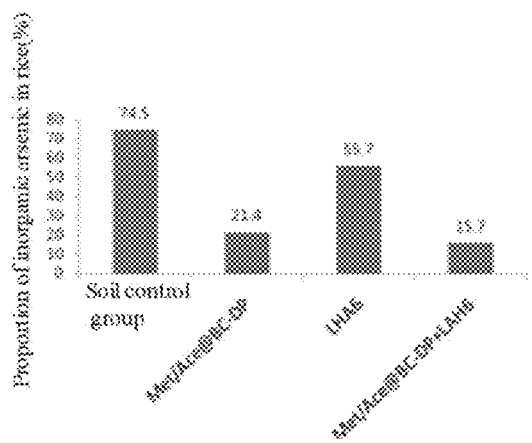
FIG. 8C shows the effect of the regulation of Met/Fat@BC-PDP combined with LHA6 strains on a proportion of inorganic arsenic in the rice.
Figure 8D:
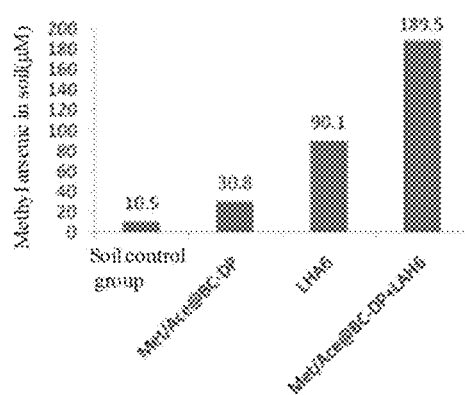
FIG. 8D shows the effect of the regulation of Met/Fat@BC-PDP combined with LHA6 strains on a methyl arsenic content of the soils.

As can be seen from FIG. 7, in the Met/Ace@BC-PDP and Met/Ace@BC-PDP-S material treatment groups, the contents of methyl arsenic in the soils reach 10.2 µM and 11.5 µM respectively, which are significantly higher than the same equivalent in single Met/Ace treatment and are also much higher than 0.04 µM in the soil control group. The results fully show that the prepared Met/Ace slow-release materials effectively improve the regulation effect of Met/Ace on microbes in soils and play a good role in production of methyl arsenic. In another aspect, the above two slow-release material treatment groups also inhibit production of methane well at 1.5 mM and 1.8 mM respectively, and the inhibitory effect is slightly better than 2.1 mM of single Met/Ace. More importantly, except for the Met/Ace@BC-PDP-S treatment group, in the other two treatments, production of methylmercury from coexisting pollutant mercury in the soils is significantly increased, reaching 0.92 µmol/kg and 0.85 µmol/kg respectively, which are much higher than the 0.08 µmol/kg in the soil control group. Unlike the methyl arsenic, production of methylmercury can lead to an exponential increase in the toxicity of mercury, thereby posing a risk. In the Met/Ace@BC-PDP-S treatment group, in addition to well inhibition on production of the methane and promotion in production of the methyl arsenic, formation of the methylmercury is further well suppressed at a level of the control group (0.09 µmol/kg), which further demonstrates that through modification with cysteine, production of the methylmercury is well inhibited, and better selectivity of production of the methyl arsenic is achieved.

Embodiment 8: Efficiency Evaluation of the Combination of Met/Fat@BC-PDP and LHA6 in Regulating Arsenic Methylation in Soil and Reducing Arsenic in Rice Based On Pot Experiment Soils of rice fields were collected from arsenic-contaminated rice fields in Xiangtan City, Hunan Province of China. During sampling, debris such as fallen leaves and animal residues on the soil surface were removed, and the surface soils were collected at a depth of 0-20 cm. The soils were brought back to a laboratory for air drying, animal and plant residues in the soils were further removed, and the soils were sieved through a 2-mm sieve. The physical and chemical properties of the test soils were as follows: pH: 5.8; soil total organic carbon: 18.57 g/kg; and total arsenic: 40.3 mg/kg. Four treatments were set in a pot experiment: control (CK), Met/Fat@BC-DP powder with a mass ratio of 0.5%, single LHA6 bacteria (100 mL of bacterial solution with a dose of $OD_{600}$=0.5), and the combination of the Met/Fat@BC-DP powder with a mass ratio of 0.5% and the LHA6 bacteria. The weight of soil per pot is about 3 kg. Before the pot experiment started, rice seeds were sterilized in a 6% NaClO solution for 30 min, washed with deionized water and then placed in a constant temperature culture room to raise seedlings, wherein the seedling raising time was about three weeks, and the rice cultivar Huang Huazhan (Guangdong Approved Rice 2005010) was used in this experiment. The fertilizer was added to each barrel 1 day before the seedlings were transplanted, wherein the adding amounts are as follows: $K_2HPO_4·3H_2O$: 0.344 g/kg; $KH_2PO_4$: 0.038 g/kg; and $CO(NH_2)_2$: 0.21 g/kg. After seedling raising of the rice was completed, the rice seedlings were transplanted to experimental pots for waterlogged cultivation. After the rice seedlings were continuously cultivated in the experimental pots in a greenhouse for 100 days and the rice was ripened, the rice was collected and placed in a blast drying oven to be fully dried, and then dry weights of above-ground plants were measured for analysis of heavy metals in plant samples; and the soils were collected, and ammonium dihydrogen phosphate was added to desorb adsorbed methyl arsenic. After the resulted soil solution passed through a 0.22-micron membrane, a form of arsenic for the extracted heavy metals was determined by HPLC-ICPMS.

As can be seen from FIG. 8A, FIG. 8B, FIG. 8C and FIG. 8D, both the Met/Ace@BC-DP treatment and LHA6 treatment groups can effectively reduce the total arsenic content in the rice from 1.5 mg/kg to 0.5 mg/kg and 0.72 mg/kg respectively, while the combination of Met/Ace@BC-DP+LHA6 further reduces the total arsenic content of rice to 0.45 mg/kg; more importantly, the combination treatment greatly reduces the proportion of inorganic arsenic in the rice, reaching 15.7%, which is significantly reduced compared with 74.5% in the control group, 21.4% in the single Met/Ace@BC-DP treatment group and 55.7% in the LHA6 treatment group. Inorganic arsenic is more toxic and is the only arsenic form that is controlled. Therefore, the combination of Met/Ace@BC-DP+LHA6 may simultaneously achieve the reduction of the total arsenic and the proportion of the inorganic arsenic in the rice; similarly, in different treatment groups, with the combination of Met/Ace@BC-DP+LHA6, the ratio of methyl arsenic in the soils may be greatly increased to 189.5 µM, which is more than 18 times higher than 10.5 µM in the soil control group. Meanwhile, with the combination of Met/Ace@BC-DP+LHA6 treatment, the yield of the rice may be effectively increased and is increased from 8.9 g/plant in the control group to 11.2 g/plant. In general, the application potential of this technology in remediating arsenic contamination in soils and reducing the risk of the arsenic in the rice is verified through the pot experiment.

The above-mentioned embodiments are preferred embodiments of the present disclosure, but the embodiments of the present disclosure are not limited by the described embodiments, and any other changes, modifications, substitutions, combinations and simplifications that do not depart from the spirit and principle of the present disclosure should be equivalent substitutions and are included within the protection scope of the present disclosure.

The invention claimed is:

1. A method for targeted regulation of soil microbes to synchronize arsenic transformation and greenhouse gas emission reduction, comprising placing a formulation comprising methionine and an organic acid salt in arsenite and/or arsenate contaminated soils simultaneously to achieve arsenic methylation and methane emission reduction synchronously;
wherein the organic acid salt is at least one of acetate, lactate or butyrate of sodium, potassium or calcium;
a molar ratio of the methionine to the organic acid salt is (1:5) to (1:50); and
an adding amount of the methionine is 0.5 to 1.5 mM based on its concentration in a reaction system.

2. A method for targeted regulation of soil microbe to synchronize arsenic transformation and greenhouse gas emission reduction, comprising placing a formulation comprising methionine and an organic acid salt in arsenite and/or arsenate contaminated soil simultaneously to achieve arsenic methylation and methane emission reduction synchronously;
wherein the organic acid salt is at least one of acetate, lactate, or butyrate of sodium, potassium, or calcium;
a molar ratio of methionine to organic acid salt is 1:10;
wherein adding an amount of methionine is 1 mM based on its concentration in the system;
wherein the methylation is at least one of monomethylation, dimethylation, or trimethylation;
and wherein the soil is soil of rice fields.

3. A preparation method for a formulation for targeted regulation of soil microbes to synchronize arsenic transformation and greenhouse gas emission reduction, wherein the formulation is a formulation comprising methionine and an organic acid salt for use according to claim 1, which is Method I or Method II as below:
Method I: mixing methionine and an organic acid salt directly; and
Method II: loading methionine and the organic acid salt into a porous biochar material
wherein the porous biochar material is prepared by the following method which comprises the following steps:
step 1: crushing a biomass raw material to particles with a particle size being less than 2 mm, washing and drying;
step 2: putting the particles obtained in step 1 in a vacuum tube furnace, heating to 500-1100° C. under the protection of nitrogen or inert gas, and keeping for 1-3 hours to prepare a pre-treated porous biochar material; and
step 3: soaking the pre-treated porous biochar material obtained in step 2 into a Tri-HCl buffer containing dopamine, or into a Tri-HCl buffer containing the dopamine and cysteine for reaction to obtain the porous biochar material;
the washing and drying described in step 1 comprises the following specific steps: soaking the obtained particles into a mixed solution of 2.5 M NaOH, 0.4 M $Na_2SO_3$ and 2.5 M $H_2O_2$, stirring evenly, transferring to a reaction kettle, and keeping at 100° C. for 10 h;

a concentration of the Tri-HCl buffer described in step 3 is 10 mM, and a pH value is 7.5±0.2;

concentrations of dopamine and cysteine in the reaction system described in step 3 are both 0.5-1.5 mM; and the reaction condition described in step 3 is stirring for reaction for 50-70 min.

4. The preparation method according to claim 3, wherein:

the Method I comprises the following specific steps: mixing methionine and the organic acid salt in a mixed solution of sodium bicarbonate, monopotassium phosphate, magnesium chloride, calcium chloride and ammonium chloride; and the Method II comprises the following specific steps: after the porous biochar material is obtained, adding methionine and the organic acid salt directly for stirring, so that methionine and the organic acid salt are fully adsorbed into the porous biochar material to form a composite system; and drying to obtain the formulation for targeted regulation of soil microbes to synchronize arsenic transformation and greenhouse gas emission reduction;

wherein the concentrations of methionine and the organic acid salt in the reaction system are calculated such that the molar ratio of methionine and the organic acid salt in the formed composite system is 1:5 to 1:50.

5. A method for targeted regulation of the soil microbes to synchronize arsenic transformation and greenhouse gas emission reduction comprising: placing the formulation of in claim 3 and a *Clostridium* bacteria in arsenite and/or arsenate-contaminated soil simultaneously to achieve arsenic methylation and methane emission reduction synchronously.

6. The method according to claim 5, wherein:

the *Clostridium* bacteria is *Clostridium sporogenes* LHA6.

\* \* \* \* \*

SEQUENCE LISTING

```
Sequence total quantity: 4
SEQ ID NO: 1            moltype = DNA   length = 23
FEATURE                 Location/Qualifiers
misc_feature            1..23
                        note = arsMF1
source                  1..23
                        mol_type = other DNA
                        organism = synthetic construct
SEQUENCE: 1
tcyctcggct gcggcaaycc vac                                              23

SEQ ID NO: 2            moltype = DNA   length = 23
FEATURE                 Location/Qualifiers
misc_feature            1..23
                        note = arsMR2
source                  1..23
                        mol_type = other DNA
                        organism = synthetic construct
SEQUENCE: 2
cgwccgccwg gcttwagyac ccg                                              23

SEQ ID NO: 3            moltype = DNA   length = 23
FEATURE                 Location/Qualifiers
misc_feature            1..23
                        note = mlas
source                  1..23
                        mol_type = other DNA
                        organism = synthetic construct
SEQUENCE: 3
ggtggtgtmg gdttcacmca rta                                              23

SEQ ID NO: 4            moltype = DNA   length = 24
FEATURE                 Location/Qualifiers
misc_feature            1..24
                        note = mcrA-rev
source                  1..24
                        mol_type = other DNA
                        organism = synthetic construct
SEQUENCE: 4
cgttcatbgc gtagttvggr tagt                                             24
```